(12) United States Patent
Liu et al.

(10) Patent No.: US 7,309,757 B2
(45) Date of Patent: Dec. 18, 2007

(54) POLYMERS FOR THE DELIVERY OF BIOACTIVE AGENTS AND METHODS OF THEIR PREPARATION

(75) Inventors: Ye Liu, Singapore (SG); Shu Wang, Singapore (SG); Chaobin He, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 514 days.

(21) Appl. No.: 10/601,262

(22) Filed: Jun. 20, 2003

(65) Prior Publication Data

US 2004/0260115 A1    Dec. 23, 2004

(51) Int. Cl.
*C08G 73/00* (2006.01)
*C08G 73/02* (2006.01)

(52) U.S. Cl. ............... 528/392; 528/288; 528/332; 528/335; 528/363; 526/310; 526/312; 526/318; 526/328; 424/78.37

(58) Field of Classification Search ............... 528/272, 528/340, 345, 392, 298, 332, 335, 363; 560/155; 526/310, 312, 318, 328; 424/78.37
See application file for complete search history.

(56) References Cited

U.S. PATENT DOCUMENTS

| | | | | |
|---|---|---|---|---|
| 4,396,760 A * | 8/1983 | Kelley | ............. | 528/345 |
| 5,180,424 A * | 1/1993 | Hutter | ............. | 524/77 |
| 6,153,596 A | 11/2000 | Liotta et al. | ............. | 514/44 |
| 6,210,717 B1 | 4/2001 | Choi et al. | ............. | 424/501 |
| 6,217,912 B1 | 4/2001 | Park et al. | ............. | 424/501 |
| 6,267,987 B1 | 7/2001 | Park et al. | ............. | 424/486 |
| 6,486,214 B1 | 11/2002 | Uhrich | ............. | 514/772.5 |
| 6,517,869 B1 * | 2/2003 | Park et al. | ............. | 424/486 |

FOREIGN PATENT DOCUMENTS

| | | | |
|---|---|---|---|
| EP | 0 002 457 A1 * | 6/1979 | |
| EP | 0 483 429 A1 | 5/1992 | |
| SU | 1016317 A * | 11/1983 | |
| WO | WO 01/97781 A1 | 12/2001 | |
| WO | WO 02/31025 A2 | 4/2002 | |
| WO | WO 02/092667 A1 | 11/2002 | |
| WO | WO 03/000776 A1 | 1/2003 | |
| WO | WO 2004/106411 A2 | 12/2004 | |

OTHER PUBLICATIONS

Lynn, D.M., Langer R. "Degradable poly(β-amino esters): Synthesis, Characterization, and Self-Assembly with Plasmid DNA", *Journal of American Chemical Society*, 2000, 122, 10761.

Lynn, D.M., Anderson D.G., Putnam D., Langer R. "Accelerated Discovery of Synthetic Transfection Vectors: Parallel Synthesis and Screening of a Degradable Polymer Library", *Journal of American Chemical Society*, 2001, 123, 8155.

Lynn, D.M., Amiji, M.M., Langer, R. "pH-Responsive Polymer Microspheres: Rapid Release of Encapsulated Materials within the Range of Intercellular pH", *Angew. Chem. Int. Ed.* 2001, 40(9), 1707.

Gao, C., Tang, W., Yan D.Y., Synthesis and Characterization of Water-Soluble Hyperbranched Poly(ester amine)s from Diacrylates and Diamines, *Journal of Polymer Science Part A: Polymer Chemistry*, 2002, 40, 2340.

Wang J., Mao, H.Q., Leong K.M., A novel Biodegradable Gene Carrier Based on Polyphospoester, *Journal of American Chemical Society*, 2001, 123, 9480.

Wang, J., Zhang, P.C., Lu, H.F., Ma, N., Wang, S., Mao, H.Q., Leong, K.M., "New polyphosphoramidate with a spermidine side chain as a gene carrier", *Journal of Controlled Release*, 2002, 83, 157.

Lim, Y.B., Kim, C.H., Kim, K., Kim, S.W., Park, J.S., "Development of a safe gene delivery system using biodegradable polymer, poly(α-(4-aminobutyl)-L-glycolic acid)", *Journal of American Chemical Society*, 2000, 122, 6524.

Lim, Y.B., Kim, S.M., Suh, H., Park, J.S., "Biodegradable, endosome disruptive, and cationic network-type polymer as a highly efficient and nontoxic gene delivery carrier", *Bioconjugate Chemistry*, 2002, 13, 952.

Oupicky, D., Parker, A.L., Seymour, L.W., "Laterally satabilized complexes of DNA with linear reducible polycations: strategy for triggered intracellular activation of DNA delivery vectors", *Journal of American Chemical Society*, 2002, 124, 8.

Liu, Y., Wu, D., Ma, Y., Tang, G., Wang, S., He, C., Chung, T., Goh, S. "Novel poly(amino ester)s obtained from Michael addition polymerizations of trifunctional amine monomers with diacrylates: safe and efficient DNA carriers", *Chemical Communications*, 2003, 20, 2630.

J. Jagur-Grodzinski, "Biomedical application of functional polymers", *Reactive & Functional Polymers*, 39 (1999) 99-138.

* cited by examiner

*Primary Examiner*—Ana Woodward
(74) *Attorney, Agent, or Firm*—Klarquist Sparkman LLP

(57) ABSTRACT

Provided is a poly(amino ester) having a polymer backbone comprising at least one secondary amine linkage and at least one tertiary amine linkage in the polymer backbone. Poly (amino ester)s are prepared via the Michael addition of a bis(acrylate ester)monomer to a diamine monomer, wherein the diamine monomer has one primary amino group and one secondary amino group, and can be end-capped by reaction with a suitable reagent. The inventive poly(amino ester)s may be used as vectors for delivery of a bioactive agent, such as DNA, to a cell.

14 Claims, 8 Drawing Sheets

POLYMERS FOR THE DELIVERY OF BIOACTIVE AGENTS AND METHODS OF THEIR PREPARATION

FIELD OF THE INVENTION

The present invention generally relates to the field of polymers and methods for their preparation. More particularly, the present invention relates to polymers that are useful for delivery of bioactive agents, such as DNA.

BACKGROUND OF THE INVENTION

There is a need for safe and efficient vectors for delivery of bioactive agents, particularly DNA. For example, the conventional approach of viral-mediated delivery of DNA has drawbacks, in that the virus may elicit an immune response in the patient or increase the risk of cancer for the patient.

A number of cationic polymers have been investigated for the delivery of bioactive agents, particularly DNA. Poly (ethylenimine) (PEI) and poly(lysine) have been widely studied as DNA condensing agents and transfection vectors and are the standards to which new polymeric vectors are often compared. However, these polymers are also associated with significant levels of cytotoxicity, and high levels of gene expression are usually realized only at a substantial cost to cell viability (see Lynn and Langer (2000) *J. Am. Chem. Soc.*, vol.122, 10761-10768). Further, PEI is not biodegradable and may not be safe for long-term treatment of a patient.

Poly(amino ester)s are attractive candidates for use as vectors for DNA delivery, in part because the y are biodegradable and cationic in physiological solutions. There have been some reports of initial investigations into synthesis and characterization of poly(amino ester)s as vectors for transfecting cells with DNA. Lynn and Langer report the synthesis of three types of poly(amino ester)s, all of which have tertiary amine linkages in the polymer backbone, are capable of binding DNA and have low cytotoxicity. However, two of these polymers are soluble only at reduced pH, i.e. not in the physiological range. Further, the reference provides no transfection assay results to show that these polymers have utility as vectors for transfecting cells with DNA. Two of these polymers were later reported in Lynn et al. (Lynn et al. (2001) *J. Am. Chem. Soc.*, vol.123, 8155-8156) as not being water-soluble and, as a result, were not tested further ELS candidates for DNA vectors.

Lynn et al. (supra) describe synthesis of a library of 140 poly(amino ester)s that were assayed for DNA-binding and transfection efficiency. Only 70 of these polymers were sufficiently water-soluble to be assayed further, another 14 did not complex DNA efficiently, and of the remaining 56 polymers, only seven polymers showed transfection efficiencies higher than that of naked DNA and three demonstrated cytotoxicity. However, the results of Lynn et al. show no clear relationship between chemical structure of the polymer and biological transfection efficiency or other properties.

Lim et al. describe a hyperbranched poly(amino ester) that has transfection efficiency comparable to PEI and low cytotoxicity (Lim et al. (2002) *Bioconjugate Chem.* vol. 13, 952). The polymer contains both primary amino and tertiary amino functional groups, which groups arm suggested by Lim et al. to be involved in DNA-binding and endosome escape of DNA, respectively. However, the method of making this hyperbranched, multi-functional polymer is inconvenient, as it involves several steps: making an $AB_2$-type monomer by reacting methyl acrylate with tris(hydroxymethyl)aminomethane, polymerizing the $AB_2$-type monomer to obtain a hyperbranched network, then attaching primary amino groups to the branched network.

Many hyperbranched polyesters have poor solubility in water. To address this problem, Gao et al. (Gao et al. (2002) *J. Polymer Sci. (Part A)* vol.40, 2340-2349) synthesized a series of poly(amino ester)s via the Michael addition of a diamine monomer containing a secondary and a primary amino group to a divinyl monomer. The resulting polymers were reported by Gao et al. to be "hyperbranched", containing between 58.2% and 75.5% of the repeating units as either being "branched" units (in which all amino groups are tertiary) or "terminal" units (reported as having an unreacted primary amino groups) and were reported to be "quite soluble in water".

Other types of cationic polymers have been suggested for use as vectors for transfection of cells with DNA, including: polyphosphates (WO 02/092667; Wang et al. (2001) *J. Am. Chem. Soc.* vol.123, 9480-9481); polyphosphoramidate bearing spermidine side chain (PPA-SP) (WO 03/000776; and Wang et al. (2002) *J. Controlled Release* vol. 83, 156-168); poly(alpha-(4-aminobutyl)-L-glycolic acid) (PAGA) (U.S. Pat. No. 6,217,912; U.S. Pat. No. 6,267, 987B1; WO 01/97781A1; and Lim et al. (2000) *J. Am. Chem. Soc.* vol. 122, 6524-6525). However, for some of the foregoing polymers, there is no data available to show that the polymers are useful as vectors for transfecting cells with DNA. For those polymers for which transfection data is available, many have drawbacks. For example, transfection efficiencies for some polymers are low relative to PEI and/or high transfection efficiencies are achieved only in the presence of chloroquine. In addition, transfection efficiency can vary depending on the type of cell being transfected, suggesting that there may be a need for a variety of different types of polymers in order to target the various cell types present in the body.

SUMMARY OF THE INVENTION

In one aspect, the present invention provides a poly (amino ester) compound having a polymer backbone comprising at least one secondary amine linkage and at least one tertiary amine linkage in the polymer backbone.

The poly(amino ester)s of the present invention may be prepared via the Michael addition of a bis(acrylate ester) monomer to a diamine monomer, wherein the diamine monomer has one primary amino group and one secondary amino group. The properties of the poly(amino ester)s of the invention can be varied by varying the bis(acrylate ester) monomer and diamine monomers used in preparing the poly(amino ester)s and the ratio thereof, for example to vary the degree of branching of the inventive poly(amino ester). If desired, the poly(amino ester) can be end-capped by reacting it with a suitable reagent.

The poly(amino ester)s of the invention may be biocompatible because they are biodegradable, die to the ester backbone linkage, and may have low cytotoxicity. As well, the poly(amino ester)s of the invention may be useful as a vector for delivering a bioactive agent, such as DNA, to a cell. Thus, in one embodiment, the invention provides poly(amino ester)s that find utility as a vector for transfecting cells with DNA in gene therapy applications.

DETAILED DESCRIPTION

Figure 1:
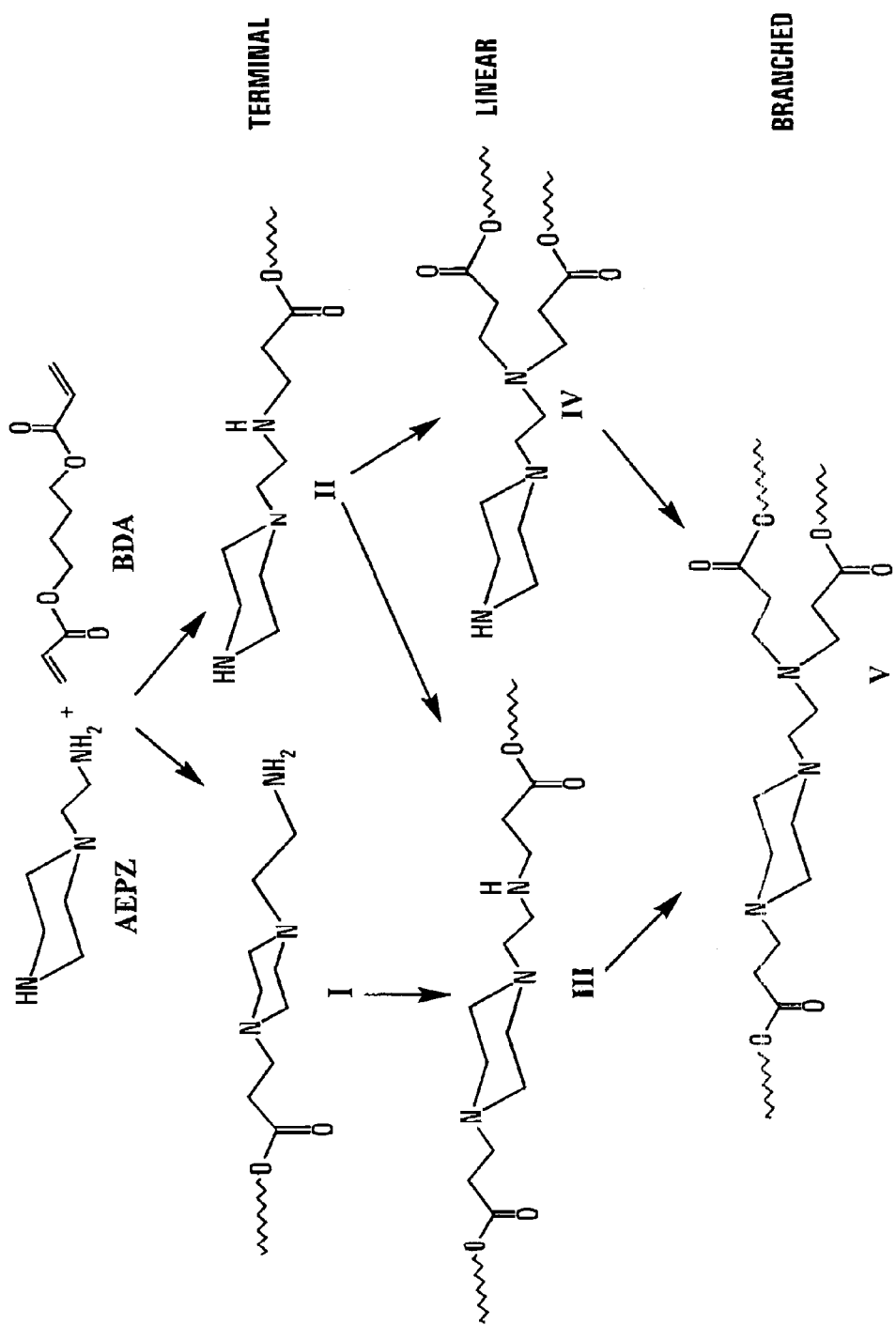
FIG. 1 is a schematic representation of five possible structures that could form by reacting a diamine monomer with a bis(acrylate ester).

The invention provides a poly(amino ester) compound having a polymer backbone comprising at least one secondary amine linkage and at least one tertiary amine linkage in the polymer backbone.

More particularly, the invention provides a compound comprising 1 to 2000 linear units independently selected from the group consisting of a linear unit of formula I:

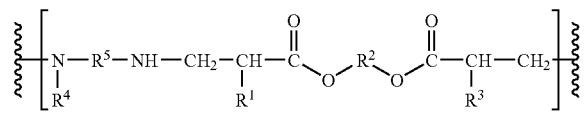

and a linear unit of formula II:

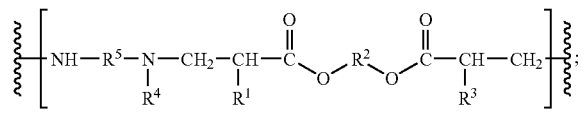

and optionally comprises one or more linear units of formula III:

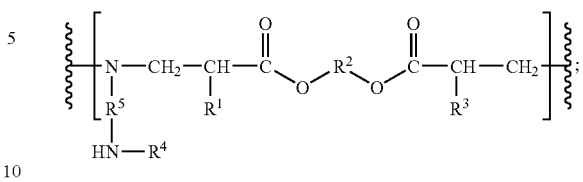

and optionally comprises one or more branched units of formula IV:

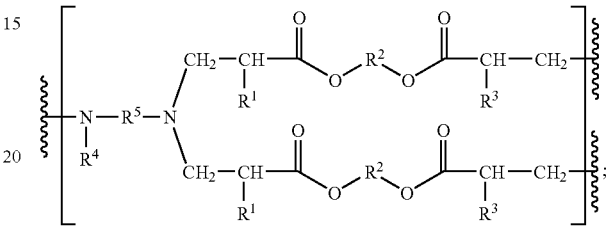

M is CH or N; and $R^7$ is unsubstituted or substituted $C_{1-28}$ alkylene optionally containing one or more heteroatoms selected from the group consisting of N, O and S; unsubstituted or substituted $C_{2-28}$ alkenylene optionally containing one or more heteroatoms selected from the group consisting of N, O and S; or unsubstituted or substituted $C_{2-28}$ alkynylene optionally containing one or more heteroatoms selected from the group consisting of N, O and S;

$R^4$ is (i) hydrocarbyl; or (ii) when $R^5$ is —$R^6$-M-$R^7$—, $R^4$ is also bonded to M and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; and $R^4$, M, $R^6$ and the nitrogen atom to which $R^4$ and $R^6$ are bonded form a saturated or unsaturated four- to twelve-membered heterocyclic ring, with the proviso that $R^1$, $R^2$, $R^3$, $R^4$ and $R^5$ cannot have a primary amino group, a secondary amino group, or a C=C double bond conjugated with a carbonyl group.

In a particular embodiment of the present invention, the invention relates to a poly(amino ester) compound comprising 1 to 2000 linear units independently selected from the group consisting of a linear unit of formula I and a linear unit of formula II and optionally wherein:

each of $R^1$ and $R^3$ is independently hydrogen, hydroxyl, halide, thiohydroxyl or hydrocarbyl;

$R^2$ is unsubstituted or substituted $C_{1-30}$ alkylene optionally containing one or more heteroatoms selected from the group consisting of N, O and S; unsubstituted car substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S;

$R^5$ is:

(i) unsubstituted or substituted $C_{1-30}$ alkylene optionally containing one or more heteroatoms selected from the group consisting of N, C and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S; or (ii) —$R^6$-M-$R^7$—, where $R^6$ is bonded to —$N(R^4)$— and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; comprising one or more linear units of formula III and optionally comprising one or more branched units of formula IV, as described above, with the proviso that when the content of linear units within the polymer backbone is between 20% and 45% and $R^2$ is ethylene, —$N(R^4)$—$R^5$—NH— cannot be 1-(2-aminoethyl)piperazinylene, N-ethylethylenediaminylene, N-methyl-1,3-propanediaminylene, piperazinylene, or 4-(aminomethyl)piperidinylene, and with the further proviso that when the content of linear units within the polymer backbone is between 20% and 45% and $R^2$ is —$(CH_2CH_2O)_nCH_2CH_2$— and n is 5, 7 or 13, —$N(R^4)$—$R^5$—NH— cannot be 1-(2-aminoethyl)piperazinylene, N-ethylethylenediaminylene, N-methyl-1,3-propanediaminylene or 4-(aminomethyl)-piperidinylene.

In the present context, the term "hydrocarbyl" means a hydrocarbon radical that may contain one or more heteroatoms and includes, without limitation, branched and unbranched alkyl, branched and unbranched alkenyl, branched and unbranched alkynyl, aryl, alkoxyl, carbamoyl, carboxyl ester, carbonyldioxyl, amide, alkylthioether, dialkylamino, trialkylamino, cyano, ureido, a substituted alkanoyl group, cyclic, cyclic aromatic, heterocyclic, and aromatic heterocyclic groups, each of which may be substituted with one or more substituents selected from the group consisting of branched and unbranched alkyl, branched and unbranched alkenyl, branched and unbranched alkynyl, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups. Thus, in the present context, the term "hydrocarbyl" includes hydrocarbon radicals that are linked to the compound via a heteroatom, for example, an alkoxy radical.

Thus, suitable values for $R^1$, $R^3$ and $R^4$ when these groups are hydrocarbyl include: substituted or unsubstituted $C_{1-30}$ alkyl, substituted or unsubstituted $C_{2-30}$ alkenyl, substituted or unsubstituted $C_{2-30}$ alkynyl, substituted or unsubstituted $C_{3-8}$ cycloalkyl, substituted or unsubstituted $C_{6-18}$ aryl, any of which may optionally contain one or more heteroatoms selected from the group consisting of N, O and S.

In the present context, the term "linear unit" refers to a structural unit of the poly(amino ester) that is covalently bonded to the polymer backbone via two covalent bonds, thereby extending the polymer backbone in a substantially linear manner. A linear unit of the invention can have a structure defined by formula I, formula II or formula III.

In the present context, the term "branched unit" refers to a structural unit of the poly(amino ester) that is covalently bonded to the polymer backbone-via three covalent bonds, thereby causing a branching of the polymer backbone. A branched unit of the invention can have a structure defined by formula IV.

In the present context, the term "terminal unit" refers to a structural unit of the poly(amino ester) that occurs at the end or terminus of a polymer chain. The terminal unit on the present poly(amino ester)s can have a structure according to the following formula V:

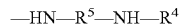

or formula VI

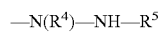

wherein $R^4$ and $R^5$ are as defined above for formulae I-IV.

Alternatively, the poly(amino ester) can be reacted with a compound of formula VII:

to form the corresponding terminal unit —$NR^9R^{10}$, wherein:

$R^9$ is:

(i) unsubstituted or substituted $C_{1-30}$ alkyl optionally containing one or more heteroatoms selected from the group consisting of N, C and S; unsubstituted car substituted $C_{2-30}$ alkenyl optionally containing one or more heteroatoms selected from the group consisting of N, O and S; or unsubstituted or substituted $C_{2-30}$ alkynyl optionally containing one or more heteroatoms selected from the group consisting of N, O and S; or (ii) —$R^{11}$-M-$R^{12}$—, where $R^{11}$ is bonded to —$N(R^{10})$— and is unsubstituted or substituted $C_{1-6}$ alkylene optionally containing one or more heteroatoms selected from the group consisting of M, O and S, or unsubstituted or substituted $C_{2-6}$ alkenylene optionally containing one or more heteroatoms selected from the group consisting of N, O and S;

M is CH or N; and $R^{12}$ is unsubstituted or substituted $C_{1-28}$ alkyl optionally containing one or more heteroatoms selected from the group consisting of N, O and S; unsubstituted or substituted $C_{2-28}$ alkenyl optionally containing one or more heteroatoms selected from the group consisting of N, O and S; or unsubstituted or substituted $C_{2-28}$ alkynyl optionally containing one or more heteroatoms selected from the group consisting of N, O and S;

$R^{10}$ is (i) hydrocarbyl or hydrogen; or (ii) when $R^9$ is —$R^{11}$-M-$R^{12}$—, $R^{10}$ is bonded to M and is unsubstituted or substituted $C_{1-3}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; and $R^{10}$, M, $R^{11}$ and the nitrogen atom to which $R^{10}$ and $R^{11}$ are bonded form a saturated or unsaturated four- to twelve-membered heterocyclic ring.

Thus, in a particular embodiment, the poly(amino ester) of the invention comprises one or more linear units of formula VIII;

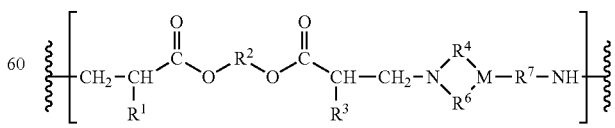

wherein:

$R^2$, $R^2$ and $R^3$ are as defined as above, and $R^4$, $R^6$ and $R^7$ are defined as above for the case when $R^5$ is —$R^6$-M-$R^7$—.

In a particular embodiment, the inventive poly(amino ester) can have the following formula IX:

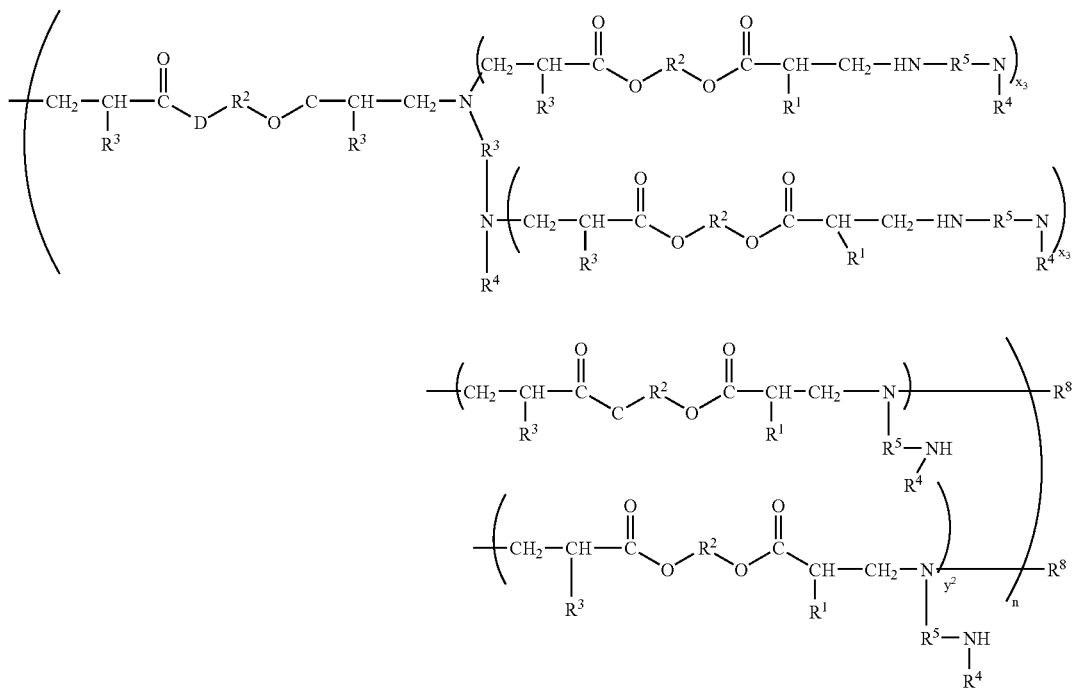

wherein:

$R^1$, $R^2$, $R^3$ $R^4$ and $R^5$ are as defined above for formulae I-IV, $R^8$ is

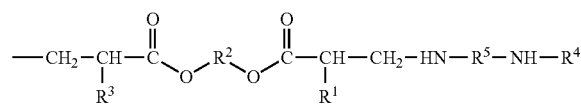

$x_1$ is an integer between 0 and 2000;
$x_2$ is an integer between 0 and 2000;
$y_1$ is an integer between 0 and 2000;
$y_2$ is an integer between 0 and 2000;
and n is an integer between 1 and 1000;

provided that $x_1$, $x_2$, $y_1$, and $y_2$ are not all zero.

In a further particular embodiment, the inventive poly(amino ester) can have the following formula X:

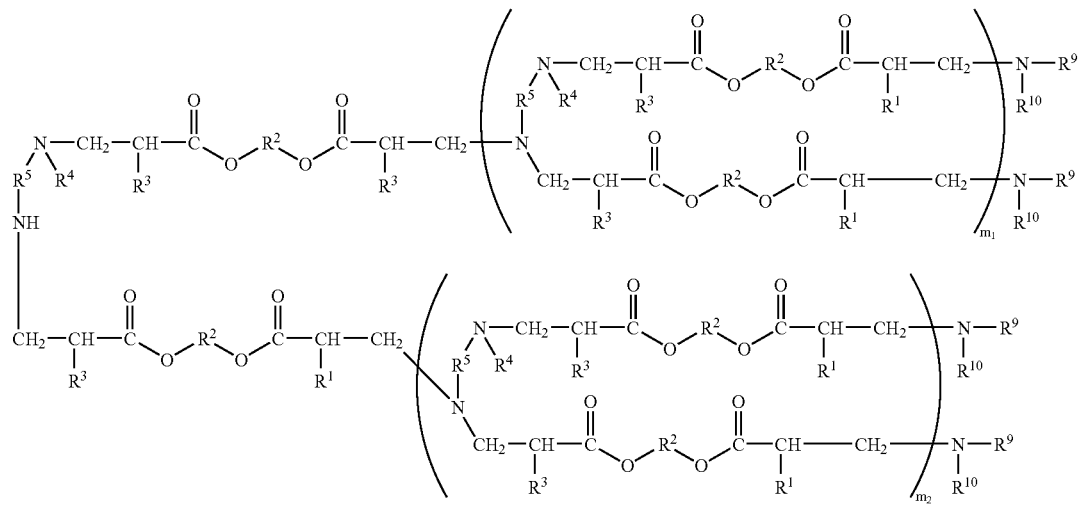

wherein:

R¹, R² R³, R⁴, R⁵, are as defined above for formulae I-IV;
R⁹ and R¹⁰ are as defined above for formula VII;
$m_1$ is an integer between 1 and 2000; and
$m_2$ is an integer between 1 and 2000.

In general, poly(amino ester)s having several secondary amino groups are preferred because secondary amines are more readily protonated than are tertiary amines and may improve the utility of the poly(amino ester), for example by enhancing water-solubility or enhancing the ability of the poly(amino ester) to interact with a bioactive agent. Secondary amino groups can be introduced into the polymer via addition of units selected from the group consisting of units of formula I, formula II, formula III, formula V, and formula VI.

Accordingly, the poly(amino ester) of the invention may contain between 1 to 2000 linear units of formula I or formula II. For example, the inventive poly(amino ester) may contain at least 0.1%, at least 1%, at least 2%, at least 3%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%)%, at least 95%, at least 97%, at least 98%, or at least 99% linear units of formula I or formula II.

The poly(amino ester) of the invention may optionally contain branched units of formula IV. For example, the inventive poly(amino ester) may contain at least 0.1%, at least 1%, at least 2%, at least 3%, at least 5%, at least 10%, at least 15%, at least 20%, at least 25%, at least 30%, at least 35%, at least 40%, at least 45%, at least 50%, at least 55%, at least 60%, at least 6',%, at least 70%, at least 75%, at least 80%, at least 8%, at least 90%, at least 95%, at least 97%, at least 98%, or at least 99% branched units of formula IV.

The poly(amino ester) of the invention will generally contain two or more terminal units.

The diamine monomer used to prepare the poly(amino ester) is asymmetrical structurally anti functionally, having a secondary amino group and a primary amino group that generally differ in reactivity. The asymmetry of the diamine gives rise to two related structures of linear units, as shown in formula I and formula II, that differ in the orientation of the diamine within the respective units.

Depending on the values selected for substituents R¹, R² and R³, the bis(acrylate) ester monomer may also be asymmetrical. Accordingly, the present invention encompasses poly(amino ester)s prepared from asymmetrical bis(acrylate) esters, i.e. where the orientation of an asymmetrical diester moiety in a structural unit can alternate along the length of a poly(amino ester).

The inventive poly(amino ester) may contain as few as 2 and as many as 2000 or more linear or branched units. Therefore, the molecular weight of the poly(amino ester) of the present invention may range from approximately 500 g/mol to approximately 600,000 g/mol, and preferably ranges from between approximately 500 to 100,000 g/mol.

FIG. 1 depicts certain structures and types of linkages that may occur in a poly(amino ester) prepared by reacting a bis(acrylate) ester, such as 1,4-butanediol diacrylate (BDA), and a diamine having a secondary and a primary amino group, such as 1-(2-aminoethyl)piperazine (AEPZ). Note that the terminal units shown in FIG. 1 have an unreacted amino group, either the original secondary amino group, or the original primary amino group (FIG. 1, structure types I and II, respectively). The linear units shown in FIG. 1 are linked to the polymer backbone through one tertiary amine linkage and lone secondary amine linkage (FIG. 1, structure type III), or through one tertiary amine linkage whereby the polymer backbone extends from a branch point formed by reaction of two molecules of bis(acrylate ester) with the primary of the diamine monomer (FIG. 1, structure type IV). The branched units shown in FIG. 1 create a branch point in the polymer backbone due to three covalent linkages that are formed by reaction of one molecule of bis(acrylate ester) monomer with the secondary amino group of the diamine monomer and further reaction of two molecules of bis (acrylate ester) monomer with the primary amino group of the diamine monomer (see FIG. 1, structure type V). Branched units therefore contain two tertiary amine linkages.

The inventive poly(amino ester) can be prepared via the Michael addition of a bis(acrylate ester) monomer and a diamine monomer that contains one secondary amino group and one primary amino group. More particularly, the poly (amino ester) of the invention may be formed by reacting a bis(acrylate ester) monomer of formula XI:

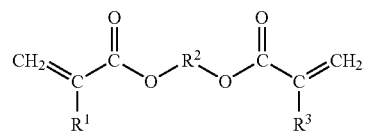

with a diamine monomer of formula XII:

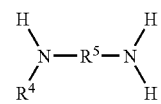

wherein R¹, R², R³, R⁴, and R⁵ are as defined above for formulae I-IV. The R groups on the diamine monomer and bis(acrylate ester) monomer must be less nucleophilic than the secondary and primary amino groups of the diamine, so that the R groups do not compete with the amino groups for reaction with the vinyl groups in the bis(acrylate ester).

In the present context, the term "diamine monomer" refers to compounds having one secondary amino group and one primary amino group but does not exclude compounds that further comprise one or more tertiary amino groups. Thus, as used herein, the term "diamine monomer" includes compounds having one secondary amino group, one primary amino group and optionally one or more tertiary amino groups.

Conveniently, there are several commercially available bis(acrylate ester) monomers and diamine monomers that can be used in the inventive method.

Bis(acrylate ester) monomers that may be used to prepare poly(amino ester)s of the present invention include, but are not limited to: 1,4-butanediol diacrylate, 1,4-butanediol dimethacrylate, 1,2-ethanediol diacrylate, 1,6-hexanediol diacrylate, 2,5-hexanediol diacrylate, poly(ethyl glycol) diacrylate, ethylene diacrylate and 1,3-propanediol diacrylate.

Diamine monomers that may be used to prepare poly (amino ester)s of the present invention include, but are not limited to: 1-(2-aminoethyl)piperazine, N-methyl ethylenediamine, 4-(aminomethyl)piperidine, 4-amino-piperidine, 3-aminopyrrolidine, N-ethylethylenediamine, N-methyl-1, 3-propanediamine, N-isopropylethylenediamine, N-hexylethylenediamine, N-butylethylenediamine, N-(2-hydroxypropyl)ethylenediamine, and N,N-diethyldiethylene triamine.

In a particular embodiment of the present method, when the bis(acrylate ester) is 1,2-ethanediol diacrylate (also known as ethylene diacrylate), the diamine monomer cannot be 1-(2-aminoethyl)piperazine, N-ethylethylenediamine, N-methyl-1,3-propanediamine, 4-(aminomethyl)-piperazine, or piperazine, and when the bis(acrylate ester) is poly(ethyl glycol)diacrylate (i.e. the compound $CH_2=CHCOO(CH_2CH_2O)_nOCCH=CH_2$, where n is 6, 8, or 14), the diamine monomer cannot be 1-(2-aminoethyl)piperazine, N-ethylethylenediamine, N-methyl-1,3-propanediamine, or 4-(aminomethyl)piperazine.

The molar ratio of diamine monomer to bis(acrylate ester) monomer can range from between about 4:1 and about 1:4, often may be between about 2:1 and about 1:2, and in many cases, will be between about 1:1 and about 1:2. Preferably, a feed molar ratio is chosen that avoids gelation.

The reaction can be carried out over a wide range of temperatures and pressures, although lower temperatures will result in longer reaction times. For example, the reaction can be carried out between about −20° C. and about 100° C. More preferably, the reaction is incubated between about −10° C. and about 90° C., more preferably between about 0° C. and about 80° C., more preferably, between about 10° C. and about 70° C., more preferably between 20° C. and 50° C. The reaction can be incubated for a period of time, say in the range of between 10 hours and 40 days. For example, when the ratio of bis(acrylate) ester to diamine used is about 1:1, the reaction is preferably incubated for between 24 hours and 96 hours, more preferably between 24 and 72 hours. When the bis(acrylate ester) is present in excess, for example when a ratio of diamine to bis(acrylate) ester used is about 1:2, longer reaction times may be required, say on the order of between about 1 day to about 40 days, preferably between about 25 days to about 40 days, and more preferably between about 30 days to about 35 days.

Preferably, the reaction is carried out in the presence of a solvent. Solvents that may be used in the method of the present invention include, but are not limited to: chloroform, dichloromethane, methyl chloride, tetrahydrofuran, methanol, ethanol, isopropanol, hexanes, toluene, benzene, carbon tetrachloride, glyme and diethyl ether.

The inventive poly(amino ester) may be used directly or may be purified prior to use. Purification can be achieved by known techniques, including, but not limited to, precipitation, crystallization, chromatography, drying under vacuum, etc. For example, the poly(amino (ester) of the invention can be precipitated with acetone containing hydrochloric acid (HCl), washed with acetone and then dried under vacuum. The poly(amino ester) of the invention can also be purified by precipitation with ether, and then washed with fresh ether and dried under vacuum.

In some cases, the poly(amino ester) is reacted with an end-capping reagent, for example of formula VII Suitable end-capping reagents include, but are not limited to, morpholine, N-methyl piperazine, N-ethyl piperazine, dimethylamine, diethylamine, and 1-methyl-4-methylamino piperidine, and benzyl-1-piperazine carboxylate.

The degree of branching in the poly(amino ester) can be varied by varying the type of monomers used and the relevant amounts thereof present in the reaction. For instance, the presence of an excess of bis(acrylate ester) monomer (say on the order of 1.5:1 to 3:1 and preferably about 2:1 bis(acrylate ester) to diamine) tends to increase the degree of branching in the poly(amino ester). Increasing the amount of bis(acrylate ester) monomer relative to diamine monomer may increase the degree of branching in the poly(amino ester), but longer reaction times may be required to complete the reaction.

In addition, a diamine monomer having a sterically hindered the secondary amino group will tend to increase the degree of branching of the poly(amino ester). Thus, diamine monomers that may be used to prepare branched poly(amino ester)s include, but are not limited to: N-ethylethylenediamine, N-isopropylethylenediamine, N-butylethylenediamine, N-(2-hydroxypropyl)ethylenediamine, N-hexylethylenediamine, and N,N-diethyldiethylene triamine. In contrast, a diamine monomer that has a relatively unhindered secondary amino group will tend to decrease the degree of branching of the poly(amino ester). Diamine monomers that may be used to prepare poly(amino ester)s that have a high degree of linearity include, but are not limited to: 4-aminopiperidine, 1-(2-aminoethyl)piperazine, N-methyl ethylenediamine, 4-(aminomethyl)piperidine, and 3-aminopyrrolidine. The structure of a poly(amino ester) obtained by the inventive method can determined by analytical methods (such as those described below).

Thus, the degree of branching of a poly-(amino ester) prepared in accordance with the present method can be varied by routine experimentation.

The structure and degree of linearity of the product obtained by the foregoing reaction can be determined by $^{13}C$ NMR spectroscopy. Briefly stated, $^{13}C$ NMR spectroscopy can be used to confirm the presence in the polymer backbone of carbon atoms that are linked to either a secondary amino group or a tertiary amino group, consistent with the poly (amino ester) of the present invention.

Figure 2A:
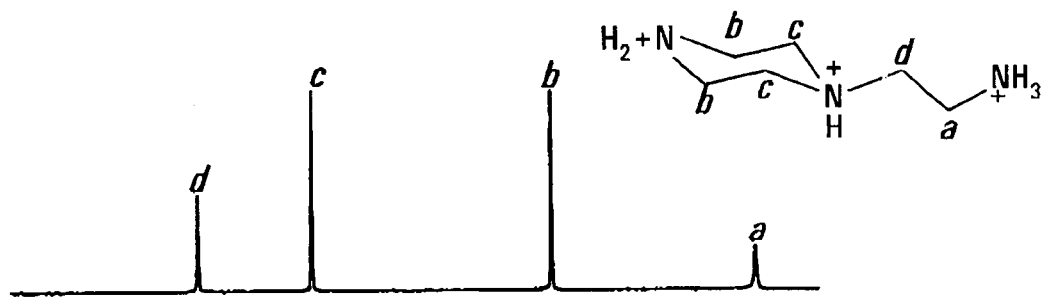
FIG. 2 is an enlarged $^{13}$C-NMR spectrum of A. protonated model compound, 1-(2-aminoethyl)piperazine (AEPZ), and B. protonated BDA-AEPZ poly(amino ester) formed by reacting AEPZ and 1,4-butanediol diacrylate (BDA).
Figure 2B:
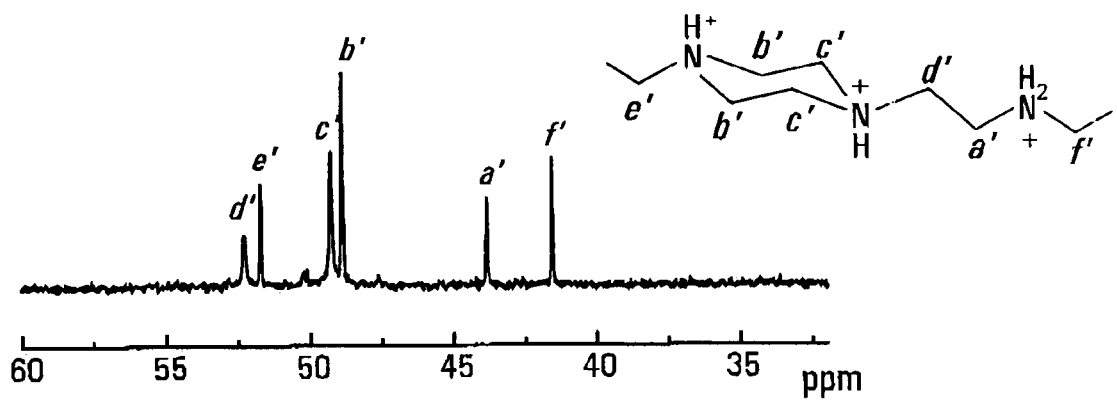
Figure 3:
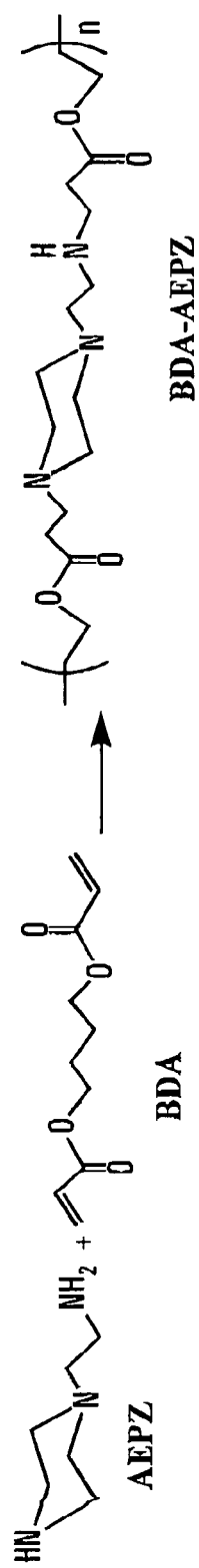
FIG. 3 is a schematic depiction of a polymerization reaction between AEPZ and BDA, resulting in poly(amino ester) containing essentially all type III linear units.

For example, $^{13}C$ NMR spectroscopy of the product of the polymerization reaction-between 1,4-butanediol diacrylate (BDA) and 1-(2-aminoethyl)piperazine (AEPZ), with the molar ratio of BDA:AEPZ at 1:1, shows six peaks (Part B of FIG. 2), indicating that the poly(amino ester) product contained either type III or type IV linear units. Particularly, two peaks corresponding to carbons linked to secondary amines (a' and f'), located at 41.5 ppm and 43.9 ppm, respectively, and four peaks corresponding to carbons linked to tertiary amines (b', c', e' and d'), located at 48.8 ppm, 49.2 ppm, 51.6 ppm and 52.7 ppm, respectively, were observed. Upon comparison to the $^{13}C$-NMR spectrum of the diamine monomer, AEPZ (Part A of FIG. 2), the results indicate that no type I terminal units, which contain a primary amino group, were obtained (peak Expected at approximately 35 ppm). As well, type V branched units or type II terminal units were not detected, as there was no detectable signal for peaks corresponding to three types of carbon linked to secondary amines and six types of carbon linked to tertiary amines in these units. The ratio of the integral intensity of the two peaks at 41.5 ppm and 43.9 ppm was determined using an inverse-gated broadband decoupled technique (INVGATE). The results, in which the ratio was found to be close to 1:1, are consistent with a poly(amino ester) in which the predominant repeating unit is a type III linear unit. Thus, the type III linear units were produced in the polymerization reaction, with no detection of type IV units, as schematically depicted in FIG. 3. The formation of type III linear poly (amino ester) may be due to increased steric hindrance of the formed secondary amine (i.e. the secondary amine formed by reaction of bis(acrylate ester) with the primary amino group of the diamine).

The poly(amino ester)s of the invention may be highly soluble, for example in aqueous solutions. As well, the inventive poly(amino ester)s can be readily degraded in aqueous solution due to hydrolysis of the ester linkages, making them very biodegradable. If non-toxic monomers are chosen as starting materials for making the poly(amino ester), then the by-products of degradation of the poly (amino ester) may be non-toxic. Thus, the linear poly(amino ester)s of the invention may be biocompatible, a property that is desirable for a poly(amino ester) intended for use as a vector for delivering bioactive agents to cells and tissues in vivo and in vitro.

The bioactive agents to be delivered by the system of the present invention may be therapeutic, diagnostic or prophylactic agents. The agent may be, for example, a small molecule, organometallic compounds, nucleic acid, protein, peptide, polynucleotide metal, an isotopically labelled chemical compound, drug, vaccine, immunological agent, etc. The agent may be described as a single entity or compound or a combination of entities or compounds.

In one embodiment, the bioactive agent is a compound with pharmaceutical activity, such as a clinically useful drug. Suitable drugs include but are not limited to: antibiotic, anti-viral agent, anesthetic, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, diuretic, cardiovascular active agent, vasoactive agent, non-steroidal anti-inflammatory agent or nutritional agent.

The bioactive agent to be delivered may also be an agent for use in diagnosis or screening. Diagnostic agents that can be delivered in vivo by the poly(amino ester) of the invention include gases, metals, commercially available imaging agents used in position emission tomography (PET), computer assisted tomography (CAT), x-ray, fluoroscopy, and magnetic resonance imaging (MRI), as well as contrast agents. Examples of suitable materials for use as contrast agents in MRI include gadolinium chelates, as well as iron, magnesium, manganese, copper, and chromium or their chelates. Examples of materials useful for CAT and x-ray imaging include iodine-based materials.

Prophylactic agents that can be delivered by the poly (amino ester) of the invention include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts.

In one embodiment of the invention, the bioactive agent to be delivered by the poly(amino ester) of the present invention is a polynucleotide. A polynucleotide may be any nucleic acid, including but not limited to, RNA and DNA. The polynucleotides may be of any size and sequence, and they may be single- or double-stranded. The polynucleotide may, for example, be greater than 1000 base pairs long or even greater than 10,000 base pairs long. In many cases, the polynucleotide will have been purified prior to use and is substantially free from contaminants, i.e. the polynucleotide is preferably more than about 50% pure, more preferably more than about 75% pure, and most preferably more than about 95% pure. The polynucleotide may be obtained by any means known in the art. Specifically, the polynucleotide may be engineered using recombinant techniques. Alternatively or in addition, the polynucleotide may be obtained from natural sources and purified from contaminating components found normally in nature. Or, the polynucleotide may be chemically synthesized in a laboratory. For example, the polynucleotide is synthesized using standard solid phase chemistry. The polynucleotide may be modified by chemical or biological means, for example to increase stability of the polynucleotide. Mehtods for modification of polynucleotides include methylation, phosphorylation, end-capping, etc. Derivatives of polynucleotides may also be used in the present invention. These derivatives include modification in the bases, sugars, and/or the phosphate linkage of the polynucleotide.

In order to deliver a bioactive agent, a poly(amino ester) of the invention is contacted with the particular agent that is to be delivered to form a complex. When the bioactive agent carries a negative charge, it may be desirable to protonate the nitrogen atoms in the poly(amino ester) (i.e. in the backbone of the poly(amino ester)) prior to contacting the poly(amino ester) with the bioactive agent, thereby providing a positively charged poly(amino ester) that can associate with negative charges present in the bioactive agent to form a complex by electrostatic attraction. As well, the monomers used to form the repeating unit may be selected to provide a poly(amino ester) with functional groups that are available to form covalent bonds with a bioactive agent. The poly (amino ester) may also form a complex by physically encapsulating the bioactive agent.

The poly(amino ester)-agent complex can be modified to include targeting agents to target a particular cell, collection of cells, nuclei, or tissues or to promote endocytosis or phagocytosis of the complex. The targeting agents may be attached to the poly(amino ester) of the present invention through covalent links, and in some cases can be added during the formation of the poly(amino ester)-agent complex. In one embodiment, the targeting agents may stay on the surface of the complex system. Examples of targeting agents include, but are not limited to, proteins, peptides, carbohydrates, glycoproteins, lipids, small molecules, antibodies, fragments of antibodies, low-density lipoproteins (LDLs), transferring, asiaglycoproteins, HIV gp120 envelope protein, receptor ligands, sialic acid, etc.

In one embodiment, a poly(amino ester)-agent complex is formed through the contacting of a polynucleotide or salt thereof with a poly(amino ester) of the invention. For this purpose, the poly(amino ester) is preferably at least partially protonated so as to electrostatically interact with the negatively charged polynucleotide. The poly(amino ester) can be protonated, for example, by solubilizing the poly(amino ester) in an aqueous solution of a pH suitable to protonate at least the secondary amines present in the poly(amino ester). The poly(amino ester)-polynucleotide complex may form nanoparticles that can then be used to deliver the polynucleotides to cells. The poly(amino ester)-polynucleotide complex system can be used to protect the polynucleotide so as to at least partially prevent degradation during the delivery and up-take process. By neutralizing the charge on the backbone of the polynucleotide, the neutral or slightly-positively-charged poly(amino ester)-polynucleotide complex may pass more easily through the hydrophobic membranes of the cell.

The poly(amino ester)-polynucleotide complex described above can be used to deliver therapeutic genes to cells of an individual in vitro or in vivo. General methods for gene therapy are known in the art. See, for example, U.S. Pat. No. 5,399,346 by Anderson it al. A biocompatible capsule for delivering genetic material is described in PCT Publication WO 95/05452 by Baetge et al. Methods of gene transfer into hematopoietic cells have also previously been reported (see Clapp, D. W., et al., Blood 78: 1132-1139 (1991); Anderson, Science 288:627-629 (2000); and, Cavazzana-Calvo et al., Science 288:669-672 (2000)). It is known that naked DNA may be introduced into cells by complexing the DNA to a cation, such as polylysine, which is coupled to a ligand for a cell-surface receptor (see for example Wu, G. and Wu, C. H. (1988) J. Biol. Chem. 263:14621; Wilson et al. (1992) J. Biol. Chem. 267:963-967, and U.S. Pat. No. 5,166,320). Binding of the DNA-ligand complex to the receptor may facilitate uptake of the DNA by receptor-mediated endocytosis. A DNA-ligand complex linked to adenovirus capsids which disrupt endosomes, thereby releasing material into the cytoplasm, may be used to avoid degradation of the complex by intracellular lysosomes (see for example Curiel et al. (1991) Proc. Natl. Acad. Sci. USA 88:8850; Cristiano et al. (1993) Proc. Natl. Acad. Sci. USA 90:2122-2126). Thus, the poly(amino ester)-nucleotide complex of the present invention may be used, either alone or in combination with a targeting agent, in receptor-mediated polynucleotide uptake, viral-mediated transfection or non-viral transfection.

Compositions containing a poly(amino ester)-polynucleotide complex of the invention may optionally contain other transfection-facilitating compounds. A number of such compositions are described in WO 93/18759, WO 93/19768, WO 94/25609, and WO 95/02397. They include spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

In various embodiments, the poly(amino ester)-agent complex of the invention may be used therapeutically in pharmaceutical compositions or medicaments to prevent or treat various diseases. The invention provides corresponding methods of medical treatment, in which a therapeutic dose of a poly(amino ester)-therapeutic agent complex is administered in a pharmacologically acceptable formulation, e.g. to a patient or subject in need thereof. Accordingly, the invention also provides pharmaceutical compositions comprising a therapeutically active (compound complexed with a poly(amino ester) of the invention and a pharmacologically acceptable excipient or carrier. The pharmaceutical composition may be soluble in an aqueous solution at a physiologically acceptable pH.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The composition can include, as noted above, an effective amount of the selected drug in combination with a pharmaceutically acceptable carrier and, in addition, may include other medicinal agents, pharmaceutical agents, carriers, adjuvants, diluents, etc.

The administration in vivo can be performed by parenteral administration, e.g., by intravenous injection including regional perfusion through a blood vessel supplying the tissue(s) or organ(s) having the target cell(s). Other means of administration can include inhalation of an aerosol, subcutaneous, intraperitoneal, or intramuscular injection, direct transfection into, e.g., bone marrow cells prepared for transplantation into an organ that is subsequently transplanted into the subject. Further administration methods can include oral administration, particularly when the complex is encapsulated, or rectal administration, particularly when the complex is in suppository form.

A "therapeutically effective amount" refers to an amount effective, at dosages and for periods of time necessary, to achieve the desired therapeutic result. A therapeutically effective amount of any particular therapeutic agent may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve a desired prophylactic result, such as preventing or inhibiting the rate of various disease onsets or progressions. A prophylactically effective amount can be determined as described above for the therapeutically effective amount. For any particular subject, specific dosage regimens may be adjusted over time according to the individual need and the professional judgement of the person administering or supervising the administration of the compositions.

As used herein "Pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such pharmaceutically acceptable carriers and excipients for pharmaceutically active substances is well known in the art. Except insofar as any conventional pharmaceutically acceptable carriers and excipients is incompatible with the active compound, use thereof in the pharmaceutical compositions of the invention is contemplated. Supplementary active compounds can also be incorporated into the compositions.

Pharmaceutical compositions typically must be sterile and stable under the conditions of manufacture and storage. The composition can be formulated as a solution, microemulsion, liposome, freeze-dried powder, spray-dried powder or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, a poly(amino ester)-agent complex can be administered in a time release formulation, for example in a composition which includes a slow release polymer. The active compounds can be prepared with carriers that will protect the compound against rapid release, such as a controlled release formulation, including implants and microencapsulated delivery systems. For this purpose, biodegradable, biocompatible polymers can be used, including but not limited to: ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the poly(amino ester)-agent complex in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred met-hods of preparation are vacuum drying, freeze-drying and spray-drying which yields a powder of the active ingredient plus any additional desired ingredient from a previously sterile-filtered solution thereof. In accordance with an alternative aspect of the invention, a poly(amino ester)-agent complex may be formulated with one or more additional compounds that enhance the solubility of the poly(amino ester)-agent complex.

In accordance with another aspect of the invention, pharmaceutical compositions of the present invention, comprising a poly(amino ester)-agent complex, may be provided in containers or commercial packages which further comprise instructions for use of the poly(amino ester)-agent complex for therapeutic use such as the prevention and/or treatment of various diseases.

Accordingly, the invention further provides a commercial package comprising a polyamino ester)-agent complex or the above-mentioned composition together with instructions for the prevention and/or treatment of a relevant disease.

All publications and patent applications cited in this specification are herein incorporated by reference as if each individual publication or patent application were specifically and individually indicated to be incorporated by reference.

The citation of any publication is for its disclosure prior to the filing date and should not be construed as an admission that the present invention is not entitled to antedate such publication by virtue of prior invention.

The following examples are offered by flay of illustration and not by way of limitation.

EXAMPLES

Materials and Reagents

Plasmid DNA (pCMV-Luc) was the kind gift of Yoshiharu Matsura (National Institute of Infectious Diseases, Tokyo, Japan). Plasmid DNA was amplified in *E. coli*, purified by Qiagen column according to the supplier's protocol (Qiagen, Hilden, Germany), re-suspended in TE (Tris 10 mM, EDTA 1 mM) buffer at a concentration of 1 mg/ml and stored in aliquots at −20° C.

1-(2-aminoethyl)piperazine (AEPZ), 1,4-butanediol diacrylate (BDA) and MTT (3-(4,5-dimethyl-thiazol-2-yl)-2,5-diphenyl tetrazolium bromide) were purchased from Aldrich (Milwaukee, Wis., USA) and used without further purification.

All other materials, including solvents, were used as received, i.e. without further purification.

General Characterization $^1$H NMR (400 MHz) and $^{13}$C NMR (100 MHz) were recorded on a Bruker DRX-400 spectrometer. Gel permeation chromatography (GPC) was carried out on a Waters 2690 apparatus with a column (Waters Ultrahydrogel 500 and 250) and a Waters 410 refractive index detector using 0.5 M acetic acid/0.5 M sodium acetate as the eluent at a flow rate of 1.0 ml/min. The molecular weights were calibrated against poly(ethylene oxide) standards.

Example 1

Synthesis and Characterization of Linear Poly(Amino Ester) BDA-AEPZ

AEPZ (20 mmol) was dissolved in 15 ml chloroform at room temperature. BDA (20 mmol) was added dropwise to the solution while stirring, followed by rinsing with 5 ml of chloroform. The reaction was incubated in a 45° C. oil bath for about 72 hours. The product was precipitated from the reaction using 400 ml of acetone containing 5 ml of hydrochloric acid (10 M). The precipitate was collected, washed with fresh acetone and dried in a vacuum oven at 50° C. for 5 days.

A water-soluble poly(amino ester) was obtained having an average molecular weight of 9900 g/mol with a wide molecular weight distribution index of 4.71 as determined by GPC.

As shown in FIG. 1, the reaction could yield five possible types of structure units. $^{13}$C NMR spectroscopy was performed to clarify the structure of product. The spectrum obtained for BDA-AEPZ (Part B of FIG. 2) was compared with the spectrum obtained for the AEPZ monomer (Part A of FIG. 2). As seen in Part B of FIG. 2, there are two types of carbon linked to secondary amines, with peaks located at 43.9 ppm and 41.5 ppm, respectively, and four types of carbon linked to tertiary amines as reflected by the peaks at 48.8 ppm, 49.2 ppm, 51.6 ppm. These results indicate that no structural units containing primary amines were obtained, ruling out the possibility of type I terminal units as products. As well, no type IV branched units or type II terminal unit-s were formed, due to no appearance of the peaks contributing to the corresponding three types of carbon linked to secondary amines and six types of carbon linked to tertiary amines. Furthermore, the ratio of the integral intensity of the two peaks at 41.5 ppm and 43.9 ppm was found to be close to 1:1 using an inverse-gated broadband decoupled technique (INVGATE), indicating that the type III linear units were obtained without the type IV linear units.

Figure 4A:
FIG. 4 shows the $^1$H-NMR spectrum of linear BDA-AEPZ after being kept in water for A. 2 hours and S. 40 days.
Figure 4B:
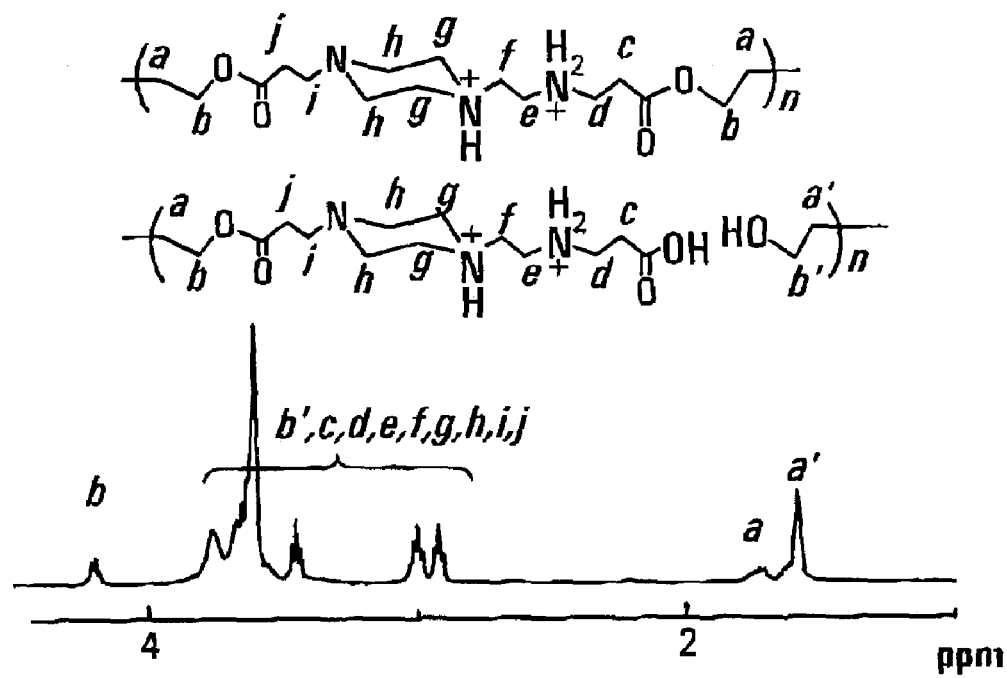
Figure 5:
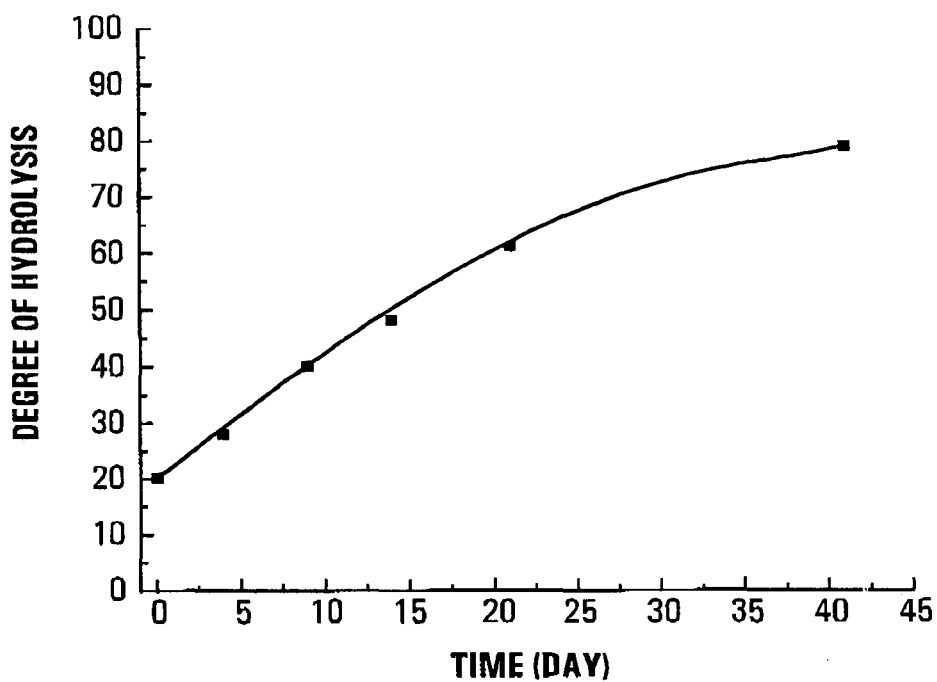
FIG. 5 is the hydrolysis profile of linear BDA-AEPZ in water.

The poly(amino ester) obtained from the polymerization of AEPZ and BDA was tested for degradability. FIG. 4 depicts $^1$H NMR spectra for BDA-AEPZ in aqueous solution. Upon hydrolysis of the ester group, the peak attributed to the proton attached to the β carbon in the 1,4-butanediol shifted from around 1.50 ppm to 1.37 ppm. Therefore, the degree of hydrolysis degree could be monitored by the change in the ratio of the integrate intensities of the two peaks, $I_{1.37}/(I_{1.50}+I_{1.37})$, as illustrated in FIG. 5.

Example 2

Formation and Analysis of DNA/Poly(Amino Ester) Complexes

Plasmid DNA (pRE-Luc) was diluted to the chosen concentration (usually 0.5-2.0 μg/μl) in 5% glucose, with vortexing. Various amounts of 0.1 M solution of BEA-AEPZ poly(amino ester) in 5% glucose was added slowly to the DNA solutions. The amount of poly(amino ester) added was calculated based on chosen weight ratios of poly(amino ester):DNA. After the solution was incubated at ambient temperature for 30 min with gentle vortexing, the formed poly(amino ester)/DNA complexes was mixed with a loading buffer and loaded onto a 1% agarose gel containing ethidium bromide. Gel electrophoresis was run at room temperature in TBE buffer at 80 V for 60 min. DNA bands were visualized by an UV (254 nm) illuminator.

Figure 6:
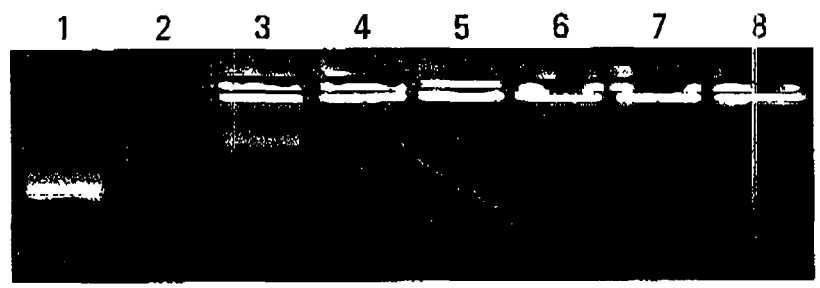
FIG. 6 illustrates the results of gel electrophoresis retardation of pRE-Luc DNA by linear BDA-AEPZ. Lane numbers correspond to different DNA/polymer weight ratios as follows: (1) 1:0 (DNA only), (2) 1:1, (3) 1:2, (4) 1:3, (5) 1:4, (6) 1:5, (7) 1:6, (8) 1:7.

Both the secondary amines and tertiary amines in BDA-AEPZ poly(amino ester) were in the protonated form at physiological pH, enabling the poly(amino ester) to interact with the negatively charged DNA. The results of the agarose gel electrophoresis, shown in FIG. 6, demonstrate that the migration of DNA was retarded completely when the weight ratios of poly(amino ester)/DNA were higher than 3:1.

Example 3

Cytotoxicity Assay of Poly(Amino Ester)

293 cells were cultured in DMEM supplemented with 10% FCS at 37° C., 10% $CO_2$, and 95% relative humidity. For the cell viability assay, polymer solutions were prepared in serum supplemented tissue culture medium. pH and osmolarity of the preparations were routinely measured and adjusted to pH 7.4 and 280-320 mosm/kg. The cells (10,000 cells/well) were seeded into 96-well microtiter plates (Nunc, Wiesbaden, Germany). After overnight incubation, the culture medium was replaced with 100 μl serial dilutions of the polymers, and the cells were incubated for another 3 h. 20 μl sterile filtered MTT (3-(4,5-dimethylthiazol-2-yl)-2,5-diphenyl tetrazolium bromide) (5 mg/ml) stock solution in phosphate buffered saline (PBS) was added to each well to reach a final MTT concentration of 0.5 mg/ml. After 4 h, unreacted dye was removed by aspiration. The formazan crystals were dissolved in 100 μl/well DMSO (BDH laboratory Supplies, England) and measured spectrophotometrically in an ELISA reader (Model 550, Bio-Rad) at a wavelength of 655 nm. The spectrophotometer was calibrated to 0 absorbance using culture medium without cells. The relative cell growth (%) related to control cells containing cell culture tedium without polymer was calculated by [A]test/[A]control×100.

Figure 7:
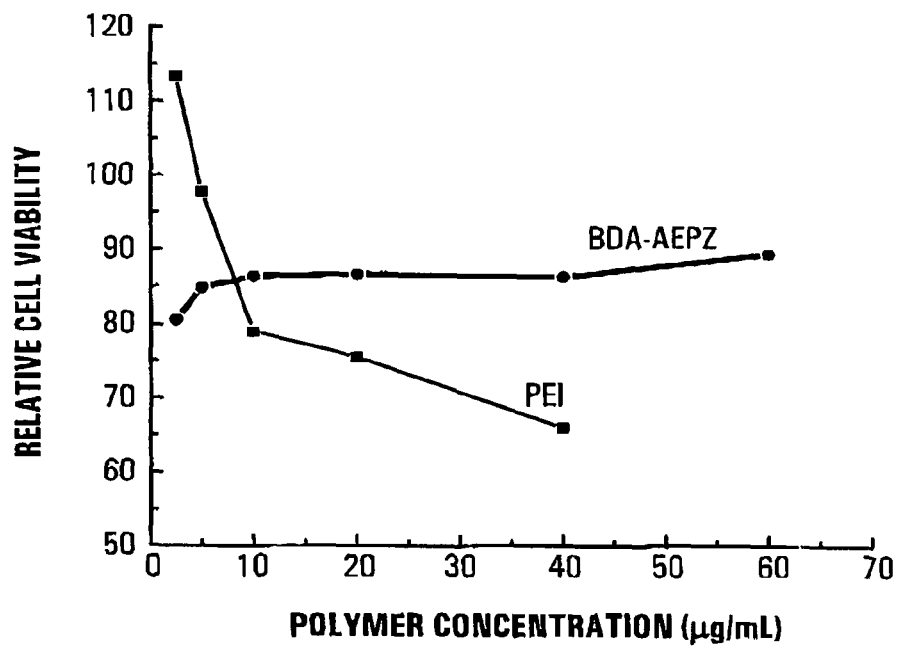
FIG. 7 is a graphical comparison of the cytotoxicity profiles of linear poly(amino ester) BDA-AEPZ with that of 25 k PEI.

FIG. 7 shows the results of the cytotoxicity assay. BDA-AEPZ poly(amino ester) had no effect gun the cell viability up to a polymer concentration of 60 μg/ml. In comparison, poly(ethyleimine) (PEI) (25 K), one of the most efficient polymers for the delivery of DNA, showed apparent toxicity as reflected by the significant decreased cell viability at a polymer concentration of 40 μg/ml.

Example 4

Cell Transfection Efficiency

The in vitro transfection efficiency of poly(amino ester) was evaluated in 293 cells using the complexes formed with BDA-AEPZ poly(amino ester) and pCAG-Luc DNA. Cells were seeded 24 h prior to transfection into 24-well plates (Becton-Dickinson, Lincoln Park, N.J.) at a density of $5\times10^4$ per well with 0.5 ml of indicated medium. At the time of transfection, the medium in each well was replaced with 300 μl of Opti-MEM. The complexes of polymer/DNA were incubated with the cells for 3 h at 37° C. The medium was replaced with 0.5 ml of fresh complete medium and cells were further incubated for 24 h. After the incubation, cells were permeabilized with 100 μl of cell lysis buffer (Promega Co., Wis.). The luciferase activity in cell extracts was measured using a luciferase assay Kit (Promega Co., Madison, Wis.) on a single-well luminometer (Berthold Lumat LB 9507, Germany) for 10 s. The light units (LU) were normalized against protein concentration in the cell extracts, which was measured using a protein assay kit (Bio-Rad Labs, Hercules, Calif.).

Figure 8:
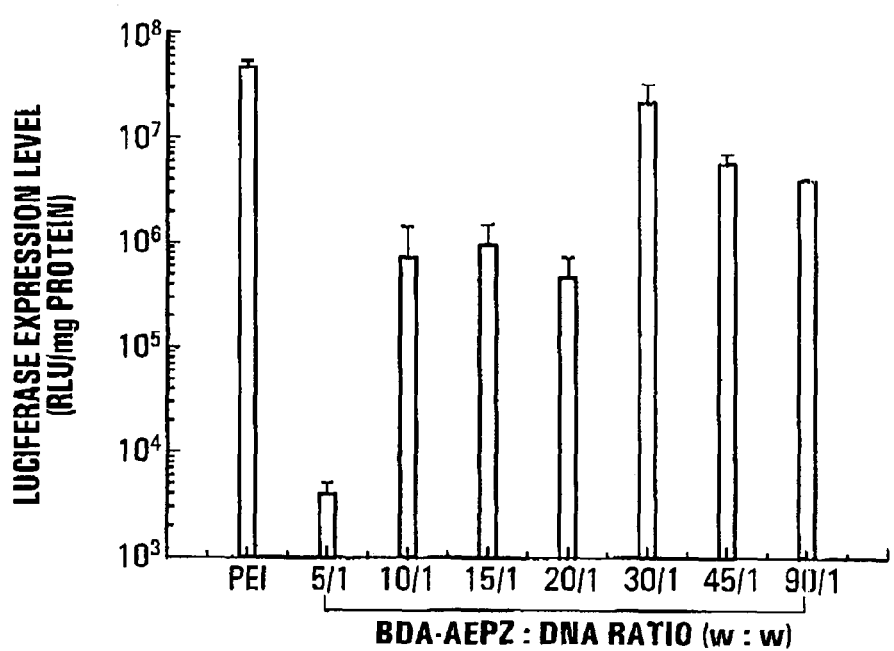
FIG. 8 is a graphical representation of the transfection efficiency of linear BDA-AEPZ/DNA complexes in 293 cells in comparison with PET-mediated transfection.

FIG. 8 displays the results for the complexes comprised of different polymer:DNA weight ratios. BDA-AEPZ poly (amino ester) yielded the highest transfection efficiency at the polymer:DNA weight ratio of 30:1, which was around 70% of control experiments employing poly(ethylenimine) (PEI) (25 k). II should be noted that the transfection efficiency measured for BDA-AEPZ poly(amino ester) was obtained in the absence of chloroquine, a commonly used weak base to enhance in vitro transfection through facilitating the release of DNA vectors from endosomes. The high transfection efficiency of BDA-AEPZ is probably due to the buffer capability resulted from the simultaneously existing secondary amines and tertiary amines, which facilitate the release of DNA from endosomes.

Example 5

Synthesis and Characterization of Branched Polymer BDA-AEPZ

AEPZ (20 mmol) was dissolved in 25 ml chloroform at room temperature BDA (40 mmol) was added dropwise to the solution while stirring, followed by rinsing with 5 ml of chloroform. The reaction was incubated in a 50° C. oil bath for about 32 days. N-methyl piperazine (MPZ) was then added to the solution to end-cap the resultant polymer. 24 h later, the product was precipitated from the reaction using 400 ml of ether. The precipitate was collected, washed with fresh ether and dried in a vacuum oven at 50° C. for 5 days.

A water-soluble polymer was obtained having an average molecular weight of 3818 g/mol with a wide molecular weight distribution index of 5.50 as determined by GPC.

Figure 9:
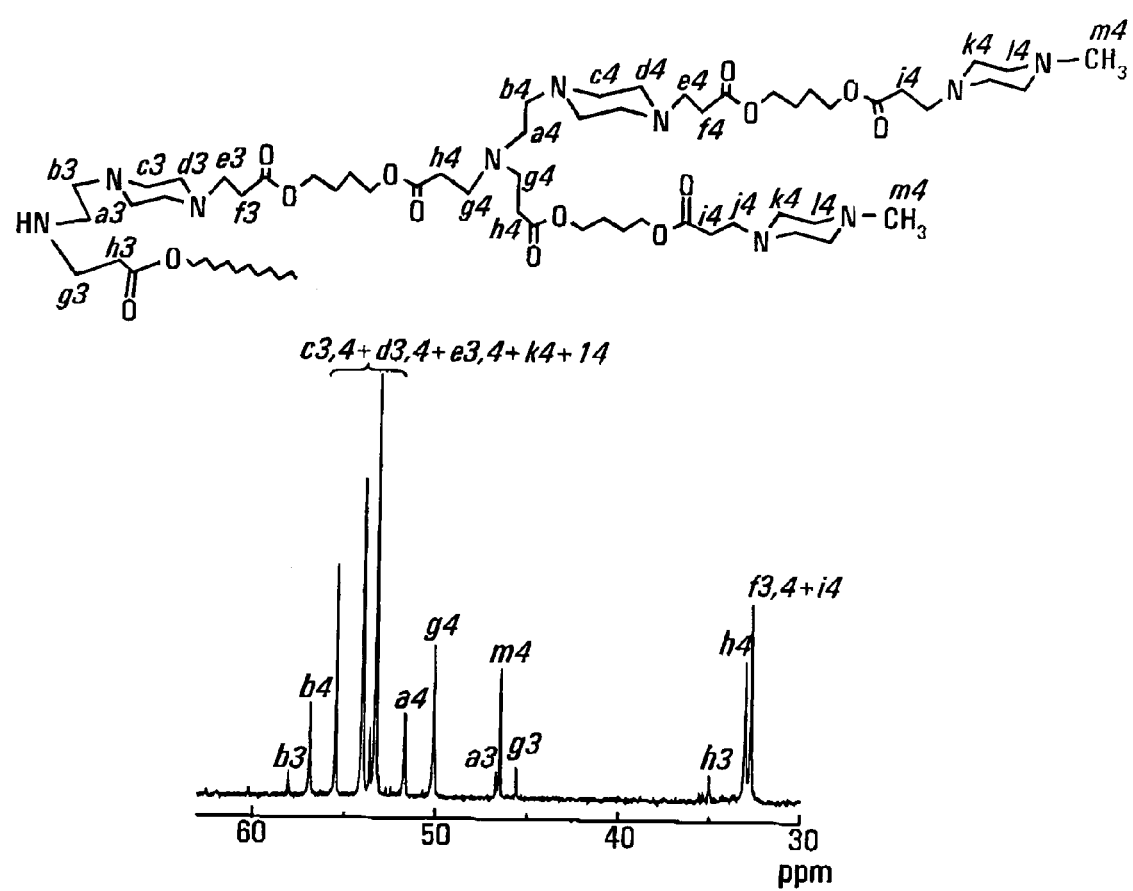
FIG. 9 is an enlarged $^{13}$C-NMR spectrum of hyperbranched BDA-AEPZ.

$^{13}$C-NMR of the product is shown in FIG. 9, which verifies the branched structure of the polymer.

Example 6

Synthesis and Characterization of Hyperbranched Polymer BDA-EEDA

N-ethyl ethylenediamine (EEDA) (20 mmol) was dissolved in 15 ml chloroform at room temperature. BDA (20 mmol) was added dropwise to the solution while stirring, followed by rinsing with 5 ml of chloroform. The reaction was incubated in a 45° C. oil bath for about 72 hours. The product was precipitated from the reaction using 400 ml of acetone containing 5 ml of hydrochloric acid (10 M). The precipitate was collected, washed with fresh acetone and dried in a vacuum oven at 50° C. for 5 days.

A water-soluble polymer was obtained having an average molecular weight of 7080 g/mol with a wide molecular weight distribution index of 3.62 as determined by GPC.

Figure 10:
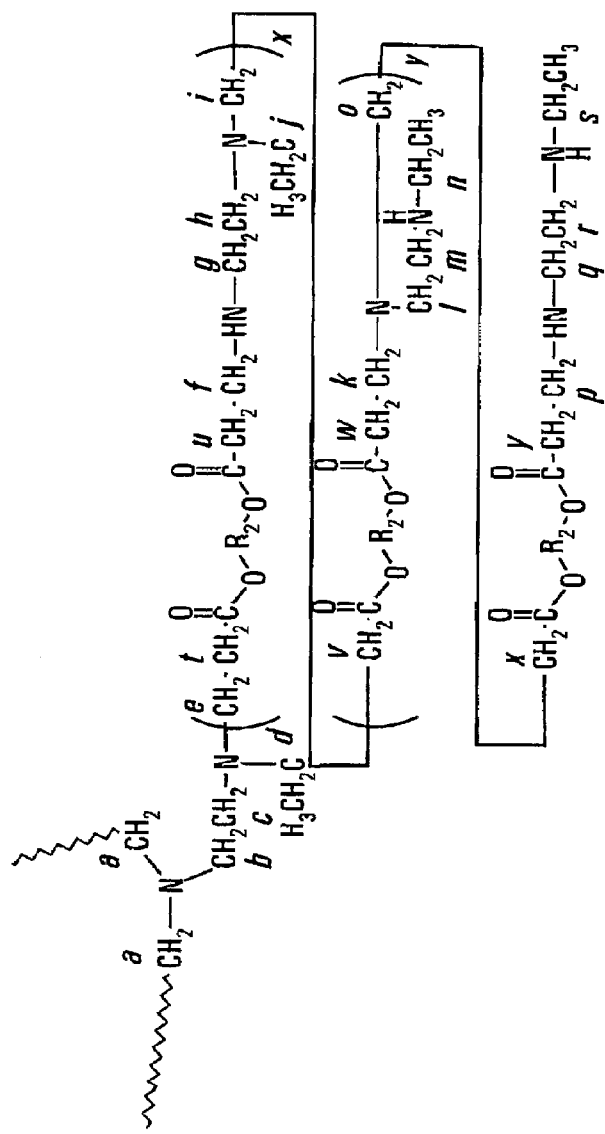
FIG. 10 is an enlarged $^{13}$C-NMR spectrum of hyperbranched protonated BDA-EEDA.
Figure 10:
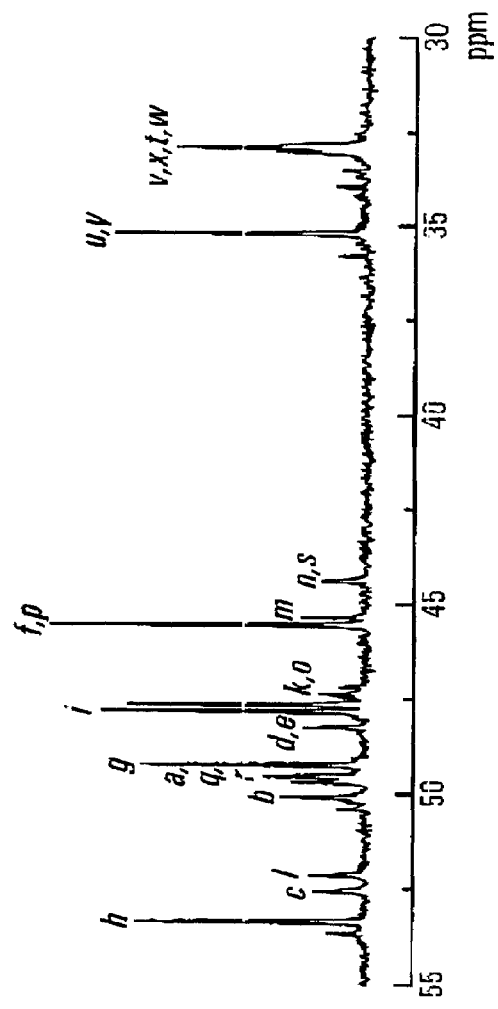

$^{13}$C-NMR of the product is shown in FIG. 10, which verifies the branched structure of the polymer.

What is claimed is:

1. A poly(amino ester) compound having a polymer backbone having at least one secondary amine linkage and at least one tertiary amine linkage in said polymer backbone, wherein said poly(amino ester) compound has no terminal primary amino group.

2. The compound of claim 1, wherein said compound comprises 1 to 2000 linear units independently selected from the group consisting of a linear unit of formula I:

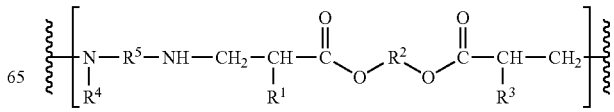

and a linear unit of formula II:

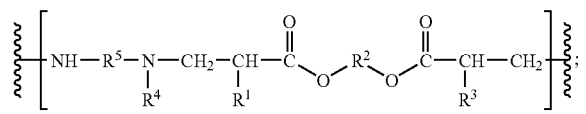

and optionally comprises one or more linear units of formula III:

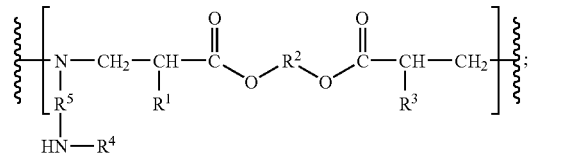

and optionally comprises one or more branched units of formula IV:

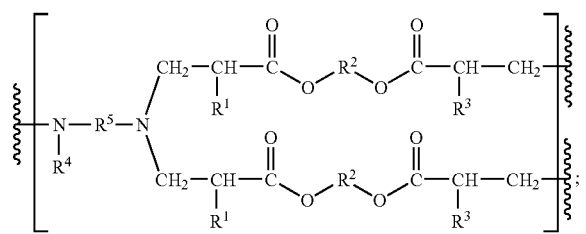

wherein:
- each of $R^1$ and $R^3$ is independently hydrogen, hydroxyl, halide, thiohydroxyl or hydrocarbyl;
- $R^2$ is unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S;
- $R^5$ is:
  - (i) unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S; or
  - (ii) —$R^6$-M-$R^7$—, where
    - $R^6$ is bonded to —N($R^4$)—and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S;
    - M is CH or N; and
    - $R^7$ is unsubstituted or substituted $C_{1-28}$ alkylene optionally containing one or more heteroatoms selected from the group consisting of N, O and S; unsubstituted or substituted $C_{2-28}$ alkenylene optionally containing one or more N, O and S; or unsubstituted or substituted $C_{2-28}$ alkynylene optionally containing one or more heteroatoms selected from the group consisting of N, O and S;
- $R^4$ is:
  - (i) hydrocarbyl; or
  - (ii) when $R^5$ is —$R^6$-M-$R^7$—, $R^4$ is also bonded to M and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; and $R^4$, M, $R^6$ and the nitrogen atom to which $R^4$ and $R^6$ are bonded form a saturated or unsaturated four- to twelve-membered heterocyclic ring,
- with the proviso that $R^1$, $R^2$, $R^3$, $R^4$ and $R^5$ cannot have a primary amino group, a secondary amino group, or a C═C double bond conjugated to a carbonyl group.

3. The compound of claim 2, wherein $R^1$ and $R^3$ are both hydrogen.

4. The compound of claim 2, wherein $R^2$ is an unsubstituted or substituted $C_{2-6}$ alkylene.

5. The compound of claim 4, wherein $R^2$ is butylene.

6. The compound of claim 4, wherein $R^2$ is ethylene.

7. The compound of claim 4, wherein $R^2$ is propylene.

8. The compound of claim 2, wherein $R^5$ is —$R^6$-M-$R^7$—, $R^4$ is also bonded to M, and $R^4$, M, $R^6$ and the nitrogen atom to which $R^4$ and $R^6$ are bonded form a saturated or unsaturated four- to twelve-membered heterocyclic ring.

9. The compound of claim 8, wherein $R^7$ is ethylene, and $R^4$, M, $R^6$ and the nitrogen atom to which $R^4$ and $R^6$ are bonded form:

10. The compound of claim 8, wherein $R^7$ is methylene, and $R^4$, M, $R^6$ and the nitrogen atom to which $R^4$ and $R^6$ are bonded form:

11. The compound of claim 2, wherein $R^5$ is a $C_{1-6}$ alkylene.

12. The compound of claim 2, wherein $R^4$ is methylene.

13. The compound of claim 2, wherein $R^4$ is selected from the group consisting of ethylene, propylene, isopropylene, 2-hydroxypropylene, 3-hydroxypropylene, butylene, hexylene, and N, N-diethylamino ethylene.

14. The compound of claim 2, wherein said compound has a molecular weight of between about 500 g/mol and 600,000 g/mol.

* * * * *

UNITED STATES PATENT AND TRADEMARK OFFICE
CERTIFICATE OF CORRECTION

PATENT NO. : 7,309,757 B2
APPLICATION NO. : 10/601262
DATED : December 18, 2007
INVENTOR(S) : Liu et al.

It is certified that error appears in the above-identified patent and that said Letters Patent is hereby corrected as shown below:

Claim 2, column 22, line 3, the following text should be inserted following "or more":
--heteroatoms selected from the group consisting of--

Column 4, line 24 to Column 5, line 13 should be replaced with the following text:
--wherein:
each of $R^1$ and $R^3$ is independently hydrogen, hydroxyl, halide, thiohydroxyl or hydrocarbyl;
$R^2$ is unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S;
$R^5$ is:
(i) unsubstituted or substituted $C_{1-30}$ alkylene optionally containing one or more heteroatoms selected from the group consisting of N, O and S; unsubstituted or substituted $C_{2-30}$ alkenylene optionally containing one or more heteroatoms selected from the group consisting of N, O and S; or unsubstituted or substituted $C_{2-30}$ alkynylene optionally containing one or more heteroatoms selected from the group consisting of N, O and S; or
(ii) $-R^6-M-R^7$, where
$R^6$ is bonded to $-N(R^4)-$ and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S;
M is CH or N; and
$R^7$ is unsubstituted or substituted $C_{1-28}$ alkylene optionally containing one or more heteroatoms selected from the group consisting of N, O and S; unsubstituted or substituted $C_{2-28}$ alkenylene optionally containing one or more heteroatoms selected from the group consisting of N, O and S; or unsubstituted or substituted $C_{2-28}$ alkynylene optionally containing one or more heteroatoms selected from the group consisting of N, O and S;

UNITED STATES PATENT AND TRADEMARK OFFICE
CERTIFICATE OF CORRECTION

| | | |
|---|---|---|
| PATENT NO. | : 7,309,757 B2 | Page 2 of 2 |
| APPLICATION NO. | : 10/601262 | |
| DATED | : December 18, 2007 | |
| INVENTOR(S) | : Liu et al. | |

It is certified that error appears in the above-identified patent and that said Letters Patent is hereby corrected as shown below:

Con't Col. 4 line 24 - Col. 5 Line 13 should read $R^4$ is (i) hydrocarbyl; or (ii) when $R^5$ is -$R^6$-M-$R^7$-, $R^4$ is also bonded to M and is unsubstituted or substituted $C_{1-6}$ alkylene optionally containing one or more heteroatoms selected from the group consisting of N, O and S, or unsubstituted or substituted $C_{2-6}$ alkenylene optionally containing one or more heteroatoms selected from the group consisting of N, O and S; and $R^4$, M, $R^6$ and the nitrogen atom to which $R^4$ and $R^6$ are bonded form a saturated or unsaturated four- to twelve-membered heterocyclic ring, with the proviso that $R^1$, $R^2$, $R^3$, $R^4$ and $R^5$ cannot have a primary amino group, a secondary amino group, or a C=C double bond conjugated with a carbonyl group.

In a particular embodiment of the present invention, the invention relates to a poly(amino ester) compound comprising 1 to 2000 linear units independently selected from the group consisting of a linear unit of formula I and a linear unit of formula II and optionally comprising one or more linear--

Column 6, line 66, "'$R^2$, $R^2$ and $R^3$'" should be changed to --$R^1$, $R^2$ and $R^3$--

Column 7, line 35, "'$R^1$, $R^2$, $R^3$ $R^4$'" should be changed to --$R^1$, $R^2$, $R^3$, $R^4$--

Signed and Sealed this

Eighteenth Day of November, 2008

JON W. DUDAS
*Director of the United States Patent and Trademark Office*